United States Patent [19]  [11] 3,933,422
Saad  [45] Jan. 20, 1976

[54] NON-STAINING KERATINIC COLORING PRODUCT

[75] Inventor: Hosny Y. Saad, Berkeley Square, N.Y.

[73] Assignee: Avon Products, Inc., Suffern, N.Y.

[22] Filed: Apr. 25, 1974

[21] Appl. No.: 464,036

Related U.S. Application Data

[63] Continuation-in-part of Ser. No. 227,601, Feb. 18, 1972, abandoned, and a continuation-in-part of Ser. No. 712,398, March 12, 1968, abandoned.

[52] U.S. Cl. .................................................. 8/10.1
[51] Int. Cl.² ........................................... A61K 7/13
[58] Field of Search ........................................ 8/10.2

[56] References Cited
UNITED STATES PATENTS 3,261,754   7/1966   Peters et al. ........................ 8/10.1
3,480,377   11/1969  Lyons .................................. 8/10.1
3,516,778   6/1970   Branner ............................... 8/10.1

Primary Examiner—Sam Rosen
Attorney, Agent, or Firm—Pennie & Edmonds

[57] ABSTRACT

A coloring composition for dyeing keratinous material comprising water, an organic dye carrier, a premetallized dye soluble in the carrier, a stain-inhibiting agent and an anionic surface active agent. The dyes are premetallized dyes and the composition includes dye carriers, anionic surface active agents, and stain inhibiting agents in an aqueous solution. The composition is effective as a semi-permanent hair dye that can be applied to hair without staining the skin of the user.

8 Claims, No Drawings

NON-STAINING KERATINIC COLORING PRODUCT

REFERENCE TO RELATED APPLICATION

This is a continuation-in-part application of Ser. No. 227,601, filed Feb. 18, 1972, and application Ser. No. 712,398, filed Mar. 12, 1968, Both applications are now abandoned.

BACKGROUND OF THE INVENTION

1. Field of the Invention

This invention relates to the dyeing of keratinous materials. More particularly, it relates to coloring compositions for producing a semi-permanent dyeing of hair for cosmetic purposes. The dyeing of the hair is accurately reproducible, nonstaining to the skin and is advantageously accomplished by directly applying the coloring composition of this invention to the hair at normal room temperature.

2. Description of the Prior Art

Coloring preparations for modifying or changing the natural hair color may be classed generally into the permanent colors and the temporary colors. In current practice permanent colors are oxidation dyes based on certain coal tar intermediates which develop color in the presence of an oxidizing agent such as hydrogen peroxide in an alkaline solution. The permanent colors are retained by the hair until the hair grows out, although the original shade may become altered as the result of frequent shampooing, perspiration, exposure to light, use of permanent waves or other chemical hair treatments.

The temporary colors are used to give color highlights to the hair, to correct yellowish streaks in gray hair, to blend in mixed gray hair and to brighten and intensify the natural hair color.

The temporary dyes are of several different types. There are acid dyes in conjunction with organic acids such as citric and tartaric, and sometimes with a surfactant. Another type is the cationic or basic dyes combined with buffering salts such as borates, citrates or phosphates. Still another type comprises the complex dyes which are formed by the interaction of acid dyes (including direct dyes) with cationic surfactants.

The dyes of all these types of temporary dyes impart color to the hair by way of forming a film on the hair surface. These films are of varying durability. Thus, the first-mentioned type, the acid dyes, can be completely removed by a single shampooing, while the second-mentioned type, the buffering cationic or basic dyes, usually last through a few shampooings.

In recent years, a demand has been created for hair colors of the temporary type--which do not require irritating oxidative dyes or high temperatures as is the case for some permanent colors--but which as well would provide a hair coloring with longer-lasting characteristics, in effect, a hair coloring which will withstand many shampoo treatments and will be semipermanent in its lasting properties. The present invention is directed towards fulfilling this need.

SUMMARY OF THE INVENTION

The principal object of this invention relates to the semi-permanent dyeing of keratinic fibers including human hair and furs at body and room temperatures, thereby preventing damage to the hair and the likelihood of toxic irritation which are associated with permanent type colors utilizing hydrogen peroxide or other oxidants in an alkaline solution while being non-staining to the skin of the user. The present invention may also be employed for dyeing either natural or synthetic polyamide fibers such as silk or animal bristles. As the dye compositions of the present invention are non-reactive, it is possible to obtain superior control over the final hair colors obtained. This is particularly so as the extent of absorption of a mixture of dyes from the coloring compositions disclosed herein is predictable and accurately reproducible giving strong level shades on normal hair, on hair which has been bleached, or on hair which has been permanent-waved.

The present invention is based upon the discovery that improved semi-permanent hair coloring compositions for dyeing at room temperature and which is non-staining to the skin of the user may be achieved through the use of an organic dye carrier in combination with an anionic surface active agent which co-assists the adsorption of the dye materials onto the outer surface of the keratinic fibers to be treated and thereafter to co-assist the penetration of the dye materials into the micropores of the fibers and in further combination with an alkoxylated lanolin or fatty alcohol to yield a composition which is non-staining to the skin of the user. Briefly stated, the hair coloring compositions of the present invention comprise a major amount of water, a premetalized dye soluble in a compatible organic dye carrier and capable of penetrating keratinic fibers, a compatible organic dye carrier for co-assisting the transfer of the dye into keratinic fibers, an anionic surface active agent and a stain retarding agent selected from alkoxylated lanolins and fatty alcohols. Preferred compatible organic dye carriers for the present invention include benzyl alcohol derivatives, alkyl phenones, cyclohexane compounds, n-nonylaldehyde, 2-phenoxyethanol, and 2-methyl-1-pentanol.

In addition to the basic essential ingredients in the coloring compositions of the present invention, namely a premetallized dye, a stain-retarding agent, a dye carrier and an anionic surfactant, it is preferable to include conventional components used in hair coloring preparations, such as a cellulose ether thickening agent, a lather-forming agent, a pH buffer and perfume for their usual and intended effect. Advantageously, the coloring compositions are buffered at a pH of from 4 to 6 although a pH of from 2 to 7 is suitable for the present invention.

DESCRIPTION OF THE PREFERRED EMBODIMENTS

A preferred formulation for the coloring compositions of this invention is listed below in Table I. (The formula below is listed in terms of parts per hundred by weight.)

TABLE I

| | |
|---|---|
| Premetallized dye | 0.1 to 10 |
| Compatible dye carrier | 1 to 10 |
| Stain inhibiting agent | 0.1 to 5 |
| Anionic surfactant | 0.01 to 5 |
| Cellulose ether (thickener) | about 1 |
| pH buffer solution | about 20 |
| Lather forming agent | 1 to 10 |
| Perfume | (in sufficient quantity) |
| Distilled water | make to 100 |

Any of the wide range of non-toxic and non-irritating premetallized dyes are suitable for the present invention to produce a wide range of desired effects. They may be chromium and/or cobalt containing dyes and their chemistry is discussed in the Journal of The Society of Dyers and Colourists, 71, pp. 705–724 (Dec. 1955). They are available commercially under such tradenames as Irgalan, Cibalan, Vialon, Ortalan and Capracyl dyes. Examples of such dyes are listed in Table II in which they have been identified by tradename and corresponding Colour Index name.

TABLE II

Cibalan Brown 2 GL (Acid Brown 224)
Irgalan Navy Blue 5RL (Acid Blue 188)
Cibalan Brown TL (Acid Brown 21)
Cibalan Bordeaux EL (Acid Red 251)
Irgalan Dark Brown 5R (Acid Brown 48)
Cibalan Bordeaux 3BL (Acid Violet 70)
Cibalan Violet RL (Acid Violet 68)

Cibalan Blue 3GL (Acid Blue 171)
Cibalan Green GL (Acid Green 43)
Cibalan Brown BL (Acid Brown 19)
Cibalan Red Brown RL (Acid Brown 226)
Cibalan Black 2BL (No C.I. name and No. yet given)
Cibalan Black 2GL (No C.I. name and No. yet given)
Cibalan Grey BL (Acid Black 60)

Preferred compatible organic dye carriers for the present invention include benzyl alcohol derivatives, alkyl phenones, cyclohexane compounds, n-nonylaldehyde and 2-methyl-1-pentanol. The most effective dye carriers for the present invention are listed below in Table III.

TABLE III

Benzyl Alcohol Derivatives

A. Alkyl Substituted Benzyl Alcohol

α,α-dimethyl benzyl alcohol
α-propyl benzyl alcohol
DL-αmethyl benzyl alcohol

B. Benzyloxyalkanols

2-Benzyloxyethanol
2-Benzyloxypropanol
2-Benzyloxybutanol

C. Esterified benzyl alcohol of $C_1$-$C_4$ carboxylic acids benzyl acetate
benzyl propionate
benzyl butyrate Alkyl Phenones acetophenone
2,4-dimethyl acetophenone
4-ethyl acetophenone
propiophenone Cyclohexane Compounds cyclohexanol
2-methyl cyclohexanol
3,5-dimethyl cyclohexanone
4-methyl cychlohexanone Equally effective are 2-phenoxyethanol, n-nonylaldehyde and 2-methyl-1-pentanol.

Any of the well-known anionic surface active agents are suitable for the present invention and such agents are listed in such sources as the annual McCutcheon's catalog "Detergents and Emulsifiers Annual." Some specific examples are sodium lauryl sulfate, triethanolamine lauryl sulfate and ethoxylated fatty alcohol sulfates. There is no criticality to the anionic surface active agent to be used.

The coloring compositions of the present invention are rendered non-staining to the skin of the user by a stain-inhibiting agent selected from polyoxyalkylene lanolins, lanolin alcohols, lanolin fatty esters, and fatty alcohols. The polyoxyalkylene lanolins should have an average degree of alkoxylation of from about 10 to 80. Examples are polyoxyethylene lanolins which are ethoxylated polymers of lanolin in which the average degree of ethoxylation ranges from 10 to 80 moles of ethylene oxide. The fatty alcohols are $C_8$-$C_{20}$ fatty alcohols with $C_{12}$-$C_{18}$ fatty alcohols being preferred. Examples of such alcohols are lauryl, myristyl, palmityl and stearyl alcohols. These agents may be used alone or in combination.

As to the cellulose ether thickening agent, any commercially available cellulose ether can be used. Examples are hydroxyethyl cellulose, carboxymethyl cellulose, hydroxypropyl cellulose, and sodium carboxymethyl cellulose.

The lather-forming agent used is preferably a mixture of lauryl diethanolamide and a dicarboxylic sodium salt derivative or coconut oil. Any lather-forming compound or composition conventionally used in hair coloring compositions can be used in the instant composition.

The pH buffers used are preferably the known phosphate, citrate and phthalate buffers suitable for the pH desired. Examples are sodium citrate; potassium acid phosphate-disodium phosphate; potassium acid phthalate-sodium hydroxide; potassium acid phosphate-sodium hydroxide; and citric acid-disodium phosphate.

The following examples illustrate the formulation and use of certain specific hair coloring compositions of the present invention. All of these compositions have the advantage of producing predictable and accurately reproducible coloring of the hair and have the important property of not staining the user's skin.

EXAMPLE 1

A hair coloring composition is formulated utilizing the constituents listed in Table IV below and the pH of the solution is adjusted by a suitable buffer to 5.0. The composition is applied to dry or wet, living human hair and left for fifteen minutes. Thereafter, the composition is shampooed out utilizing conventional soaps and the hair is found to be colored a medium brown while an examination of the scalp shows no staining. (The formula listed below is in terms of parts per hundred by weight).

TABLE IV

| | |
|---|---|
| 2-Benzyloxyethanol | 4.0 |
| Cibalan brown TL (Acid Brown 21) | 1.0 |
| Triethanolamine lauryl sulfate | 1.0 |
| Buffer Solution | 20.0 |
| Carboxymethyl cellulose | 1.0 |
| Lauryl alcohol | 1.0 |
| Perfume | (in sufficient quantity) |
| Distilled water | make to 100 |

EXAMPLE 2

A hair coloring composition is formulated utilizing the consituents listed below in Table V and the pH is adjusted to 40 The composition is applied to dry or wet human hair and left for 15 minutes. After the coloring composition is shampooed, the hair is found to be colored a bordeaux shade. The skin of the user is not stained. (The formula listed below is in terms of parts per hundred by weight).

TABLE V

| | |
|---|---|
| α,α-Dimethylbenzyl alcohol | 1.0 |
| Cibalan Bordeaux EL (Acid Red 251) | 0.5 |
| Sodium laurylsulfate | 0.1 |
| Hydroxyethyl cellulose | 1.0 |
| Myristyl alcohol | 1.0 |
| Buffer Solution | 20.0 |
| Glycerin | 5.0 |
| Perfume | (in sufficient quantity) |
| Distilled water | make to 100 |

EXAMPLE 3

A hair coloring composition is formulated from the constituents listed below in Table VI and the pH is adjusted to 60 The composition is applied to dry or wet human hair in the conventional manner and produces a dark brown coloring. The skin of the user is not stained. (The formula listed below is in terms of parts per hundred by weight).

TABLE VI

| | |
|---|---|
| Lanolin alcohol | 2.0 |
| DL-α-Methyl benzyl alcohol | 2.0 |
| Dicarboxylic coconut derivative sodium salt | 0.5 |
| Polyoxyethylene (40) lanolins | 0.3 |
| Lauryl diethanolamide | 0.3 |
| Triethanolamine lauryl sulfate | 2.0 |
| Irgalan Dark Brown 5R (Acid Brown 48) | 1.0 |
| Buffer solution | 20.0 |
| Hydroxyethyl cellulose | 1.0 |
| Perfume | (in sufficient quantity) |
| Distilled water | make to 100 |

EXAMPLE 4

A hair coloring composition is formulated as indicated below in Table VII and the pH adjusted to 60 After applying the hair coloring composition to dry or wet human hair in the conventional manner, the hair is found to have been colored a dark brown. The skin of the user is not stained. (The formula listed below is in terms of parts per hundred by weight).

TABLE VII

| | |
|---|---|
| Lauryl alcohol | 2.0 |
| Benzyl acetate | 2.0 |
| Dicarboxylic coconut derivative sodium salt | 0.5 |
| Polyoxy ethylene lanolin (Lanogel 41) | 0.3 |
| Lauryl diethanolamide | 0.3 |
| Triethanolamine lauryl sulfate | 2.0 |
| Irgalan dark brown 5R (Acid Brown 48) | 1.0 |
| Hydroxyethyl cellulose | 2.5 |
| Buffer solution | 20.0 |
| Perfume | (in sufficient quantity) |
| Distilled water | make to 100 |

Although the above specification describes preferred hair coloring compositions and the method of making them in accordance with the teachings of the present invention, it is to be understood that various changes may be made without departing from the scope of the invention as set forth in the following claims.

What is claimed is:

1. An aqueous hair coloring composition that is non-staining to the skin consisting essentially of:
   a. a major amount of water;
   b. from about 0.1 to about 10% by weight of a premetallized dye soluble in a compatible organic dye carrier and capable of penetrating keratinic fibers;
   c. from about 0.1 to about 10% by weight of a compatible organic dye carrier for coassisting the transfer of said dye into keratinic fibers, said dye carrier selected from the group consisting of:
      1. a benzyl alcohol derivative selected from the group consisting of benzyl alcohols, $C_1$-$C_4$ carboxylic acid esterified benzyl alcohol and benzyloxyalkanols;
      2. an alkyl phenone;
      3. an oxygen substituted cyclohexane selected from the group consisting of cyclohexanols and cyclohexanones;
      4. n-nonylaldehyde;
      5. 2-methyl-1-pentanol;
      6. 2-phenoxy-ethanol;
   d. from about 0.1 to about 5% by weight of an anionic surface active agent; and
   e. from about 0.1 to about 5% by weight of a skin stain inhibiting agent selected from the group consisting of polyoxyalkylene (10 - 80) lanolins, lanolin alchols, lanolin fatty esters and $C_8$-$C_{20}$ fatty alcohols.

2. An aqueous hair coloring composition as set forth in claim 1 in which said skin stain inhibiting agent is a polyoxyalkylene lanolin which has an average degree of alkoxylation of from about 10 to about 80.

3. An aqueous hair coloring composition as set forth in claim 2 in which said organic dye carrier is an alkyl phenone selected from the group consisting of acetophenone, 2,4-dimethyl acetophenone, 4-ethyl acetophenone and propiophenone.

4. An aqueous hair coloring composition as set forth in claim 1 in which said organic dye carrier is an alkyl phenone selected from the group consisting of acetophenone, 2,4-dimethyl acetophenone, 4-ethyl acetophenone and propiophenone.

5. An aqueous hair coloring composition as set forth in claim 2 in which said organic dye carrier is an α-substituted benzyl alcohol selected from the group consisting of α,α-dimethyl benzyl alcohol, α-propyl benzyl alcohol and DL-α-methyl benzyl alcohol.

6. An aqueous hair coloring composition as set forth in claim 1 in which said organic dye carrier is an α-substituted benzyl alcohol selected from the group consisting of α,α-dimethyl benzyl alcohol, α-propyl benzyl alcohol and DL-α-methyl benzyl alcohol.

7. An aqueous hair coloring composition as set forth in claim 2 in which the organic dye carrier is an oxygen substituted cyclohexane selected from the group consisting of 3,5-dimethyl cyclohexanone, 4-methyl cyclohexanone, cyclohexanol and 2-methyl cyclohexanol.

8. An aqueous hair coloring composition as set forth in claim 1 in which the organic dye carrier is an oxygen substituted cyclohexane selected from the group consisting of 3,5-dimethyl cyclohexanone, 4-methyl cyclohexanone, cyclohexanol and 2-methyl cyclohexanol.

* * * * *